United States Patent [19]

Berg et al.

[11] Patent Number: 5,092,965

[45] Date of Patent: * Mar. 3, 1992

[54] SEPARATION OF 4-METHYL-2-PENTANONE FROM ACETIC ACID BY EXTRACTIVE DISTILLATION WITH DMFA

[75] Inventors: Lloyd Berg, 1314 S. Third Ave., Bozeman, Mont. 59715; Marc W. Paffhausen, Bozeman, Mont.

[73] Assignee: Lloyd Berg, Bozeman, Mont.

[*] Notice: The portion of the term of this patent subsequent to Jun. 20, 2006 has been disclaimed.

[21] Appl. No.: 702,515

[22] Filed: May 2, 1991

[51] Int. Cl.⁵ .................. B01D 3/40; C07C 45/83; C07C 51/44
[52] U.S. Cl. .................. 203/51; 203/56; 203/60; 203/61; 203/62; 203/63; 203/64; 562/608; 568/410
[58] Field of Search .................. 203/60, 51, 64, 56, 203/61, 63, 62; 568/410; 562/608

[56] References Cited

U.S. PATENT DOCUMENTS

| | | | |
|---|---|---|---|
| 3,013,954 | 12/1961 | Pacoud et al. | 203/62 |
| 3,228,985 | 1/1966 | Carpenter et al. | 568/410 |
| 4,551,208 | 1/1985 | Bott et al. | 203/60 |
| 4,840,707 | 6/1989 | Berg et al. | 203/60 |
| 4,861,436 | 8/1989 | Berg et al. | 203/51 |
| 4,994,151 | 2/1991 | Berg et al. | 203/51 |

*Primary Examiner*—Wilbur Bascomb, Jr.

[57] ABSTRACT

4-Methyl-2-pentanone cannot be easily separated from acetic acid by distillation because of the closeness of their boiling points. 4-Methyl-2-phentanone can be readily removed from acetic acid by extractive distillation. Typical effective agents are dimethylformamide (DMFA); DMFA and m-toluic acid; DMFA, p-toluic acid and isobutyl heptyl ketone.

1 Claim, No Drawings

SEPARATION OF 4-METHYL-2-PENTANONE FROM ACETIC ACID BY EXTRACTIVE DISTILLATION WITH DMFA

This application is related to application Ser. No. 07/484,264, abandoned.

FIELD OF THE INVENTION

This invention relates to a method for separating 4-methyl-2-pentanone from acetic acid using DMFA either alone or admixed with other higher boiling organic compounds as the agents in extractive distillation.

DESCRIPTION OF PRIOR ART

Extractive distillation is the method of separating close boiling compounds or azeotropes by carrying out the distillation in a multi-plate rectification column in the presence of an added liquid or liquids mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Acetic acid and 4-methyl-2-pentanone boil only 2.5 Celsius degrees apart and thus have a relative volatility of only 1.06. Table 1 shows the boiling point relationship for these two compounds at 640 mm.HG pressure. From Table 1, it can be seen that in concentrations of 4-methyl-2-pentanone below 77 percent, the boiling point changes only 0.5° C. and further separation by rectification becomes virtually impossible. Although the overall relative volatility is 1.06, in this region it is almost 1.0, just about as difficult to separate as an azeotrope.

TABLE 1

| Boiling Points of 4-Methyl-2-pentanone - Acetic Acid Mixtures at 640 mm. Hg. | | |
|---|---|---|
| % 4-Methyl-2-pentanone | % Acetic Acid | Boiling Point, °C. |
| 100 | 0 | 109 |
| 90 | 10 | 110 |
| 77 | 23 | 111 |
| 50 | 50 | 111.2 |
| 40 | 60 | 111.2 |

TABLE 1-continued

| Boiling Points of 4-Methyl-2-pentanone - Acetic Acid Mixtures at 640 mm. Hg. | | |
|---|---|---|
| % 4-Methyl-2-pentanone | % Acetic Acid | Boiling Point, °C. |
| 33 | 67 | 111.3 |
| 23 | 77 | 111.4 |
| 10 | 90 | 111.4 |
| 0 | 100 | 111.5 |

Extractive distillation would be an attractive method of effecting the separation of 4-methyl-2-pentanone from acetic acid if agents can be found that (1) increase the relative volatility of 4-methyl-2-pentanone to acetic acid and (2) are easy to recover from acetic acid, that is, form no azeotrope with acetic acid and boil sufficiently above acetic acid to make separation by rectification possible with only a few theoretical plates.

Extractive distillation typically requires the addition of an equal amount to twice as much extractive agent as the acetic acid- water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with acetic acid otherwise it will form a two-phase azeotrope with the acetic acid in the recovery column and some other method of separation will have to be employed.

OBJECTIVE OF THE INVENTION

The object of this invention is to provide a process or method of extractive distillation that will enhance the relative volatility of 4-methyl-2-pentanone from acetic acid in their separation in a rectification column. It is a further object of this invention to identify organic compounds which are stable, can be separated from acetic acid by rectification with relatively few plates and can be recycled to the extractive distillation column and reused with little decomposition.

TABLE 2

| Effective Extractive Distillation Agents Containing DMFA | | | | |
|---|---|---|---|---|
| Compounds | Ratios | | Relative Volatilities | |
| Dimethylformamide (DMFA) | 2 | 12/5 | 3.2 | 3.3 |
| DMFA, Adipic acid | (½)[2] | (3/5)[2] | 2.0 | 2.3 |
| DMFA, Acetyl salicylic acid | " | " | 1.3 | 1.9 |
| DMFA, Cinnamic acid | " | " | 1.9 | 1.6 |
| DMFA, Decanoic Acid | " | " | 1.1 | 1.2 |
| DMFA, Glutaric acid | " | " | 1.2 | 1.3 |
| DMFA, Heptanoic acid | " | " | 1.5 | 1.7 |
| DMFA, Hexanoic acid | " | " | 1.7 | 1.3 |
| DMFA, Pelargonic acid | " | " | 1.5 | 1.4 |
| DMFA, Neodecanoic acid | " | " | 2.3 | 1.9 |
| DMFA, Octanoic acid | " | " | 1.1 | 2.1 |
| DMFA, Salicylic acid | " | " | 1.1 | 1.5 |
| DMFA, Sebacic acid | " | " | 1.2 | 1.5 |
| DMFA, m-Toluic acid | " | " | 2.4 | 1.2 |
| DMFA, p-Toluic acid | " | " | 2.3 | 1.7 |
| DMFA, Adipic acid, Diethylene glycol dibenzoate | (⅓)[3] | (2/5)[3] | 2.2 | 2.1 |

TABLE 2-continued

Effective Extractive Distillation Agents Containing DMFA

| Compounds | Ratios | | Relative Volatilities | |
|---|---|---|---|---|
| DMFA, Acetyl salicylic acid, Ethylene glycol phenyl ether | " | " | 1.1 | 1.4 |
| DMFA, Azelaic acid, Propiophenone | " | " | 2.2 | 1.1 |
| DMFA, Cinnamic acid, Diethyl maleate | " | " | 2.1 | 1.3 |
| DMFA, Decanoic acid, Benzyl benzoate | " | " | 1.1 | 1.2 |
| DMFA, Glutaric acid, Diethylene glycol diethyl ether | " | " | 2.9 | 2.2 |
| DMFA, Hexanoic acid, Ethyl benzoate | " | " | 3.1 | 1.2 |
| DMFA, Heptanoic acid, Benzyl ether | " | " | 2.4 | 1.7 |
| DMFA, Pelargonic acid, Methyl benzoate | " | " | 1.5 | 1.6 |
| DMFA, Neodecanoic acid, 2-Octanone | " | " | 1.3 | 1.2 |
| DMFA, Octanoic acid, Cyclohexanone | " | " | 1.5 | 2.4 |
| DMFA, Salicylic acid, Ethyl acetoacetate | " | " | 2.8 | 1.6 |
| DMFA, Sebacic acid, Ethylene glycol methyl ether acetate | " | " | 1.7 | 1.6 |
| DMFA, m-Toluic acid, Isobutyl heptyl ketone | " | " | 2.4 | 1.4 |

TABLE 3

Potential Agents Which Are Ineffective

Compounds

Dimethylformamide (DMFA), Azelaic acid
DMFA, Itaconic acid
DMFA, Itaconic acid, Ethylene glycol butyl ether acetate
DMFA, p-tert. Butyl benzoic acid
DMFA, p-tert. Butyl benzoic acid, Ethylene glycol ethyl ether acetate
DMFA, Benzoic acid
DMFA, Benzoic acid, Butyl ether
DMFA, o-Toluic acid
DMFA, o-Toluic acid, Ethyl phenyl ether

TABLE 4

Data From Run Made in Rectification Column

| Agent | Column | Time, hrs. | Weight % Ketone | Weight % Acetic acid | Relative Volatility |
|---|---|---|---|---|---|
| 33% DMFA, 33% Pelargonic acid, 33% Methyl benzoate | Overhead | 0.5 | 84.6 | 15.4 | 1.57 |
| | Bottoms | | 33.3 | 66.7 | |
| 33% DMFA, 33% Pelargonic acid, 33% Methyl benzoate | Overhead | 1 | 92.3 | 7.7 | 1.64 |
| | Bottoms | | 46.2 | 53.8 | |

SUMMARY OF THE INVENTION

The objects of the invention are provided by a process for separating 4-methyl-2-pentanone from acetic acid which entails the use of dimethylformamide (DMFA), either alone or admixed with higher boiling organic compounds as the agent in extractive distillation.

DETAILED DESCRIPTION OF THE INVENTION

We have discovered that dimethylformamide (DMFA), either alone or admixed with other high boiling organic compounds, will effectively increase the relative volatility of 4-methyl-2-pentanone to acetic acid and permit the separation of 4-methyl-2-pentanone from acetic acid by rectification when employed as the agent in extractive distillation. Table 2 lists DMFA and its mixture and the approximate proportions that we have found to be effective. The data in Table 2 was obtained in a vapor-liquid equilibrium still. In each case, the starting material was a 50-50 wt. % mixture of 4-methyl-2-pentanone and acetic acid. The ratios are the parts by weight of extractive agent used per part of 4-methyl-2-pentanone-acetic acid mixture. The relative volatilities are listed for each of the two ratios employed. The compounds which are effective when used in mixtures with DMFA are adipic acid, acetyl salicylic acid, cinnamic acid, decanoic acid, glutaric acid, heptanoic acid, hexanoic acid, pelargonic acid, neodecanoic acid, octanoic acid, salicylic acid, sebacic acid, m-toluic acid, p-toluic acid, diethylene glycol dibenzoate, ethylene glycol phenyl ether, propiophenone, diethyl maleate, benzyl benzoate, diethylene glycol diethyl ether, ethyl benzoate, benzyl ether, methyl benzoate, 2-octanone, cyclohexanone, ethyl acetoacetate, ethylene glycol methyl ether acetate and isobutyl heptyl ketone.

The two relative volatilities shown in Table 2 correspond to the two different ratios investigated. For example, in Table 2, two parts of DMFA mixed with one part of 4-methyl-2-pentanone-acetic acid mixture give a relative volatility of 3.2, 12/5 parts of DMFA give 3.3. One half part of DMFA mixed with one half part of adipic acid with one part of the 4-methyl-2-pentanone-acetic acid mixture give a relative volatility of 2.0, 3/5 parts of DMFA plus 3/5 parts of adipic acid give 2.3. One third part of DMFA plus 1.3 part of adipic acid plus 1.3 part of diethylene glycol dibenzoate with one part of the 4-methyl-2-pentanone-acetic acid mixture gives a relative volatility of 2.2, with 2/5 parts, these three give a relative volatility of 2.1. In every example in Table 2, the starting material is a 4-methyl-2-pentanone-acetic acid mixture which possesses a relative volatility of about 1.11.

One of the mixtures, DMFA, pelargonic acid and methyl benzoate, listed in Table 2 and whose relative volatility had been determined in the vapor-liquid equilibrium still, was then evaluated in a glass perforated plate rectification column possessing 5.3 theoretical plates and the results listed in Table 4. The data in Table 4 was obtained in the following manner. The charge was 200 grams of 50% 4-methyl-2-pentanone 50% acetic acid and after a half hour of operation in the 5.3 theoretical plate column to establish equilibrium, a mixture containing 33% DMFA, 33% pelargonic acid and 33% methyl benzoate at 85° C. and 20 ml/min. was pumped in. The rectification was continued with sampling of overhead and bottoms after 1.2 hour. The analysis is shown in Table 4 and was 84.6% 4-methyl-2-pentanone, 15.4% acetic acid in the overhead and 33.3% 4-methyl-2-pentanone, 66.7% acetic acid in the bottoms which gives a relative volatility of 1.57 of 4-methyl-2-pentanone to acetic acid. After one hour of continuous operation, the overhead was 92.3% 4-methyl-2-pentanone, 7.7% acetic acid, the bottoms was 46.2% 4-methyl-2-pentanone, 53.8% acetic acid which is a relative volatility of 1.64. Table 3 contains several potential extractive distillation agents which might be expected to be successful but which proved to be ineffective.

THE USEFULNESS OF THE INVENTION

The usefulness or utility of this invention can be demonstrated by referring to the data presented in Tables 1, 2 and 3. All of the successful extractive distillation agents show that 4-methyl-2-pentanone and acetic acid can be separated from their mixtures by means of distillation in a rectification column and that the ease of separation as measured by relative volatility is considerable. Without these extractive distillation agents little improvement will occur in the rectification column. The data also show that the most attractive agents will operate at a boilup rate low enough to make this a useful and efficient method of recovering high purity 4-methyl-2-pentanone from any mixture with acetic acid. The stability of the compounds used and the boiling point difference is such that complete recovery and recycle is obtainable by a simple distillation and the amount required for makeup is small.

WORKING EXAMPLES

Example 1

Forty grams of 4-methyl-2-pentanone-acetic acid mixture and 40 grams of DMFA were charged to a vapor-liquid equilibrium still and refluxed for 16 hours. Analysis indicated a vapor composition of 42.1% 4-methyl-2-pentanone, 57.9% acetic acid, a liquid composition of 69.8% 4-methyl-2-pentanone, 30.2% acetic acid which is a relative volatility of 3.2.

Example 2

Eighty grams of a 4-methyl-2-pentanone-acetic acid mixture, 25 grams of DMFA and 25 grams of adipic acid were charged to the vapor-liquid equilibrium still and refluxed for 12 hours. Analysis indicated a vapor composition of 50% 4-methyl-2-pentanone, 50% acetic acid, a liquid composition of 32.9% 4-methyl-2-pentanone, 67.1% acetic acid which is a relative volatility of 2.0. Five grams of DMFA and five grams of adipic acid were added and refluxing continued for another six hours. Analysis indicated a vapor composition of 55.6% 4-methyl-2-pentanone, 44.4% acetic acid, a liquid composition of 35.3% 4-methyl-2-pentanone, 64.7% acetic acid which is a relative volatility of 2.3.

Example 3

Eighty grams of a 4-methyl-2-pentanone-acetic acid mixture, 17 grams of DMFA, 17 grams of adipic acid and 17 grams of diethylene glycol dibenzoate were charged to the vapor-liquid equilibrium still and refluxed for 18 hours. Analysis indicated a vapor composition of 54.9% 4-methyl-2-pentanone, 45.1% acetic acid, a liquid composition of 35.5% 4-methyl-2-pentanone, 64.5% acetic acid which is a relative volatility of 2.2. Three grams each of DMFA, adipic acid and diethylene glycol dibenzoate were added and refluxing continued for another nine hours. Analysis indicated a vapor composition of 50% 4-methyl-2-pentanone, 50% acetic acid, a liquid composition of 32.4% 4-methyl-2-pentanone, 67.6% acetic acid which is a relative volatility of 2.1.

Example 4

A glass perforated plate rectification column was calibrated with ethylbenzene and p-xylene which possesses a relative volatility of 1.06 and found to have 5.3 theoretical plates. A solution comprising 100 grams of 4-methyl-2-pentanone nad 100 grams of acetic acid was placed in the stillpot and heated. When refluxing began, an extractive agent comprising 33% DMFA, 33% pelargonic acid and 33% methyl benzoate was pumped into the column at a rate of 20 ml/min. The temperature of the extractive agent as it entered the column was 85° C. After establishing the feed rate of the extractive agent, the heat input to the 4-methyl-2-pentanone and acetic acid in the stillpot was adjusted to give a total reflux rate of 10–20 ml/min. After one half hour of operation, the overhead and bottoms samples of approximately two ml. were collected and analysed by gas chromatography. The overhead analysis was 84.6% 4-methyl-2-pentanone, 15.4% acetic acid. The bottoms analysis was 33.3% 4-methyl-2-pentanone, 66.7% acetic acid. Using these compositions in the Fenske equation, with the number of theoretical plates in the column being 5.3, gave an average relative volatility of 1.57 for each theoretical plate. After one hour of total operating time, the overhead and bottoms samples were again taken and analysed. The overhead composition was 92.3% 4-methyl-2-pentanone, 7.7% acetic acid and the bottoms composition was 46.2% 4-methyl-2-pentanone, 53.8% acetic acid. This gave an average relative volatility of 1.64 for each theoretical plate. These data are presented in Table 4.

We claim:

1. A method for recovering 4-methyl-2-pentanone from a mixture of 4-methyl-2-pentanone and acetic acid which comprises distilling a mixture of 4-methyl-2-pentanone and acetic acid in a rectification column in the presence of about one part of an extractive agent per part of 4-methyl-2-pentanone-acetic acid mixture, recovering 4-methyl-2-pentanone as overhead product and obtaining the acetic acid and the extractive agent from the stillpot, wherein said extrcative agent consists of dimethylformamide and at least one material selected from the group consisting of glutaric acid, m-toluic acid, p-toluic acid, diethylene glycol dibenzoate, ethylene glycol phenyl ether, propiophenone, diethyl maleate, diethylene glycol diethyl ether, benzyl ether, ethyl acetoacetate, ethylene glycol methyl ether acetate and isobutyl heptyl ketone.

* * * * *